United States Patent
Ginis et al.

(10) Patent No.: US 11,771,551 B2
(45) Date of Patent: Oct. 3, 2023

(54) METHOD TO DESIGN AND MANUFACTURE AN INTRAOCULAR LENS

(71) Applicant: VOPTICA S.L., Murcia (ES)

(72) Inventors: Harilaos Ginis, Murcia (ES); Pablo Artal Soriano, Murcia (ES)

(73) Assignee: VOPTICA S.L., Murcia (ES)

( * ) Notice: Subject to any disclaimer, the term of this patent is extended or adjusted under 35 U.S.C. 154(b) by 0 days.

(21) Appl. No.: 16/916,728

(22) Filed: Jun. 30, 2020

(65) Prior Publication Data

US 2021/0353405 A1 Nov. 18, 2021

(30) Foreign Application Priority Data

May 14, 2020 (ES) .................. ES202030449

(51) Int. Cl.
*A61F 2/16* (2006.01)
(52) U.S. Cl.
CPC ............ *A61F 2/164* (2015.04); *A61F 2/1627* (2013.01); *A61F 2002/1681* (2013.01); *A61F 2240/004* (2013.01)
(58) Field of Classification Search
CPC .................... A61F 2/164; A61F 2/1627; A61F 2002/1681; A61F 2204/004
See application file for complete search history.

(56) References Cited

U.S. PATENT DOCUMENTS

| | | |
|---|---|---|
| 4,504,982 A | 3/1985 | Burk |
| 8,235,525 B2 | 8/2012 | Lesage et al. |
| 10,010,407 B2 | 7/2018 | Rosen et al. |

(Continued)

FOREIGN PATENT DOCUMENTS

| | | |
|---|---|---|
| AU | 2007247491 B2 | 12/2010 |
| CA | 2 587 432 C | 5/2006 |
| WO | 2005/098518 A1 | 10/2005 |

*Primary Examiner* — Jerrah Edwards
*Assistant Examiner* — Aren Patel
(74) *Attorney, Agent, or Firm* — LADAS & PARRY LLP

(57) ABSTRACT

Method to design manufacture an intraocular lens, comprising an optical part and haptics part, in which the optical part comprises an anterior surface with negative refractive power and a posterior surface with positive refractive power, in which in order to determine the refractive power D of the anterior surface of the optical part and the refractive power D' of the posterior surface of the optical part the following steps are performed:

- a plurality of light rays are provided over the normal eye, both on the optical axis (1001) and forming different angles (714, 715, 716) with respect to the optical axis (1001),
- for each light ray with its angle the axial length of the eye and the refractive power of the cornea are measured,
- determination of the shape of the retina (200) through a mathematical fit to an aspherical surface that contains the measured points,
- calculation of the arc length S that goes from the intersection of the optical axis with the retina (200) of the eye to the intersection of the light ray with the retina (200) of the eye for each angle, as a function of the shape of the retina (200) and the angle of the light ray,
- fit of the refractive power D of the anterior surface of the optical part and refractive power D' of the posterior surface of the optical part using ray tracing optimization in a pseudophakic eye model.

6 Claims, 8 Drawing Sheets

(56) References Cited

U.S. PATENT DOCUMENTS

| | | | |
|---|---|---|---|
| 2009/0175525 A1* | 7/2009 | Farrer | G01B 11/2513 |
| | | | 382/131 |
| 2010/0211170 A1* | 8/2010 | Liao | A61F 2/16 |
| | | | 623/6.34 |
| 2011/0082542 A1* | 4/2011 | Norrby | A61B 3/1035 |
| | | | 623/6.12 |
| 2016/0302660 A1* | 10/2016 | Buhren | A61B 3/1005 |
| 2016/0345825 A1* | 12/2016 | Murai von Bunau | A61F 2/16 |
| 2017/0196682 A1* | 7/2017 | Lawu | A61F 2/1637 |
| 2021/0030531 A1* | 2/2021 | Ambati | A61F 2/1637 |

* cited by examiner

METHOD TO DESIGN AND MANUFACTURE AN INTRAOCULAR LENS

FIELD OF INVENTION

The present invention refers to a method to design and manufacture an intraocular lens as used in ophthalmology, especially for cataract surgery, providing a field curvature optimized in the eye.

BACKGROUND OF THE INVENTION

The crystalline lens (eye lens) is a complicated structure and its function has been a topic of study for centuries. It exhibits a gradient in its refractive index ranging from about 1.390 at the lens surface to about 1.409 at its core. Said gradient is achieved by a variable concentration of crystallin proteins in the cytoplasm of the lens' fiber cells. Despite the high amount of proteins, the healthy eye lens shows a remarkable transparency due to the compact distribution of the proteins. Furthermore, the eye lens has aspherical surfaces, which reduces spherical aberration in the eye. Additionally, the design of the human eye allows for the image formation at the periphery to be optimized in terms of aberrations and field curvature with respect to the shape of the retina.

Cataracts are a pathological condition in which the natural lens has lost its transparency and the image formation at the retina is deteriorated mainly due to light scattering and aberrations. In most cases, to solve said problem, cataract surgery is performed through which the deteriorated eye lens is extracted from the eye and a specific implant (an IntraOcular Lens IOL) is implanted as a replacement of the extracted lens to substitute its refractive power.

Intraocular lenses have been used in ophthalmology for longer than half a century. Since then, the implantation of IOLs has become the most common and successful surgery, not only in the field of ophthalmology, but medicine in general. The implant is chosen such that it provides the required refractive power to optimize the focus on the fovea, the location with largest resolution of the retina, substituting the patient's natural lens. The central visual field of the pseudophakic eye (with the eye lens substituted by an IOL) is characterized by a good image quality, limited in practice in its totality due to the post-operative sphero-cylindrical refractive error, or in some cases, and depending on the implant used, due to the introduction of spherical aberration.

In most cases, optical quality in the periphery of the visual field is not considered as one of the most important aspects in the design of an IOL, since, for large eccentricities at the retina, the number of photoreceptive cells is smaller and the neuronal convergence is larger. Due to these physiological limitations of the retina, the IOLs have been designed concentrating exclusively in the image quality at the central part of the retina (for small angles close to the fovea), without considering the effects on the far periphery of the visual field. While the natural eye lens has properties adapted to the shape of the retina, the IOLs do not take this phenomenon into account. However, there are specific applications where the quality of peripheral vision might have a great impact in vision quality, such as the detection of movement direction of visual patterns or even simple activities such as the detection of small peripheral objects. More important is the fact that the change of the nodal points of the eye is associated with a general change of the magnification and its dependence on field angle (distortion).

Although the peripheral performance of the pseudophakic eye has not been studied in detail, there is evidence that proves that said change in the perceived shape of objects in the far periphery may have implications in the spatial orientation and safety of the patients.

There are multiple types of IOLs implemented in patent and scientific literature. For example, document U.S. Pat. No. 4,504,982A (Burk) describes a generic aspherical lens for intraocular implantation that has a biconvex shape. However, there is no consideration for peripheral vision in its design.

CA2587432C (Norrby) describes a method to select an intraocular lens, that involves exclusively optical and anatomical measurements that are used later on to calculate the power and spherical aberration of the required IOL. Said invention does not consider the possible dispositions for the quality of the peripheral image and, furthermore, does not include the patients' pre-operative subjective evaluation (psychophysical).

AU2007247491B2 (Gerlach) describes a method to design an intraocular lens with given asphericity to compensate corneal aberrations, considering the potential eccentricity of the pupil. The same principles are described in a later document from the same inventors (U.S. Pat. No. 8,235,525B2 (Lesage)). The previously mentioned invention does not include dispositions for peripheral image quality.

Document WO2005098518A1 (Piers) describes a hybrid lens with at least a diffractive element used to control total longitudinal chromatic aberration of the eye.

Document US10010407B2 (Rosen), describes an IOL design to improve the specific aberrations of the wavefront such as coma or astigmatism for the peripheral visual field for angles up to 40 degrees, without reference to the quality or distortion of the peripheral image.

Currently there is a need in the market for intraocular lenses that provide a close correspondence to the natural eye in terms of geometrical distortion, specially in the far peripheral field.

SUMMARY OF THE INVENTION

The object of the present invention is to provide a method to design and manufacture an intraocular lens that resembles the imaging properties of the crystalline lens, specially with respect to the geometrical distortion of the image in the far periphery of the visual field.

The invention provides a method to design and manufacture an intraocular lens, which comprises an optical part and a haptics part, in which the optical part comprises an anterior surface with negative refractive power and a posterior surface with positive refractive power, the anterior surface being the closest to the eye's cornea once it is implanted in the eye, and the posterior surface being the closest to the eye's retina once it is implanted in the eye, which comprises the following steps:
 to provide the haptics part,
 to provide the optical part, and
 to join the haptics part with the optical part,
in which to determine the refractive power D of the anterior surface of the optical part and the refractive power D' of the posterior surface of the optical part the following steps are carried out:
 a plurality of light rays are provided over the natural eye, both on the optical axis and with different angles with respect to the optical axis, for each light ray with its angle the eye's axial length is measured, including the intersection point between the light ray with the eye's retina, and the refractive power of the cornea, determination of the retina's shape using a mathematical fit to an aspherical surface containing the measured points, calculation of the arc length S that goes from the intersection of the optical axis with the eye's retina to the intersection of the light ray with the eye's retina for each angle, as a function of the retina's shape and the angle of the light ray, and fit of the refractive power D of the anterior surface of the optical part and the refractive power D' of the posterior surface of the optical part using ray tracing optimization in a pseudophakic eye model, to provide both an optical approach for the central vision on the optical axis as well as a length S for each field angle, so that they are like those of the normal eye.

The intraocular lens manufactured through the method of the present invention allows to obtain a refractive power suitable to provide a good focus in the central visual field, and a refractive power balance between the anterior element and the posterior element such that the central and peripheral magnification of the pseudophakic eye is similar to that of the intact (natural) eye.

Other characteristics and advantages of the present invention will be derived from the detailed description that follows from an illustrative embodiment of its object in relation to the figures that are attached.

BRIEF DESCRIPTION OF THE DRAWINGS

Next the object of the present invention will be illustrated in a non-limitative manner, with reference to the accompanying drawings, in which.

DETAILED DESCRIPTION OF THE INVENTION

Figure 1:
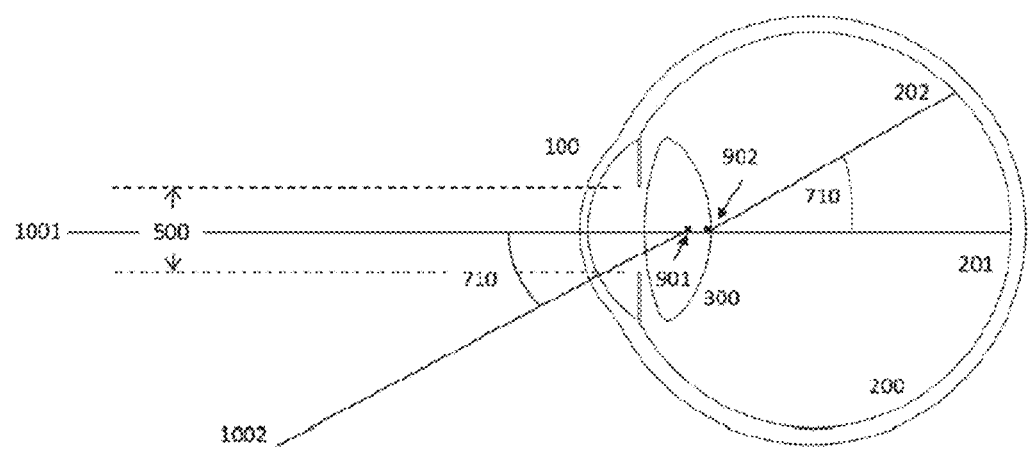
FIG. 1 shows a transversal section of a human eye and the focus of objects in the center of the visual field and at a certain angle in the periphery of the visual field.

FIG. 1 shows a transversal section of the eye, where light enters through the pupil (500) and passes through the cornea (100) and the eye lens (300) to be focused in the retina (200). The nodal points (901 and 902) are situated over the optical axis (1001) such that a ray over the oblique axis (1002) goes to the nodal point (901) after the refraction in the cornea (100) and the eye lens (300) and the ray has a direction emerging from the second nodal point (902). For a natural human eye looking at infinity (distant vision) these points are located close to the posterior surface of the eye lens (300). In this condition if the oblique axis is forming an angle (710) with the optical axis, then the angle of propagation of the light after refraction in the cornea (100) and eye lens (300) is also equal to that angle (710). It is evident that the position of the nodal points (901 and 902) and specially the second nodal point (902) determines the position (202) in which the peripheral objects situated at a certain angle (710) are formed in the retina (200).

Figure 2:
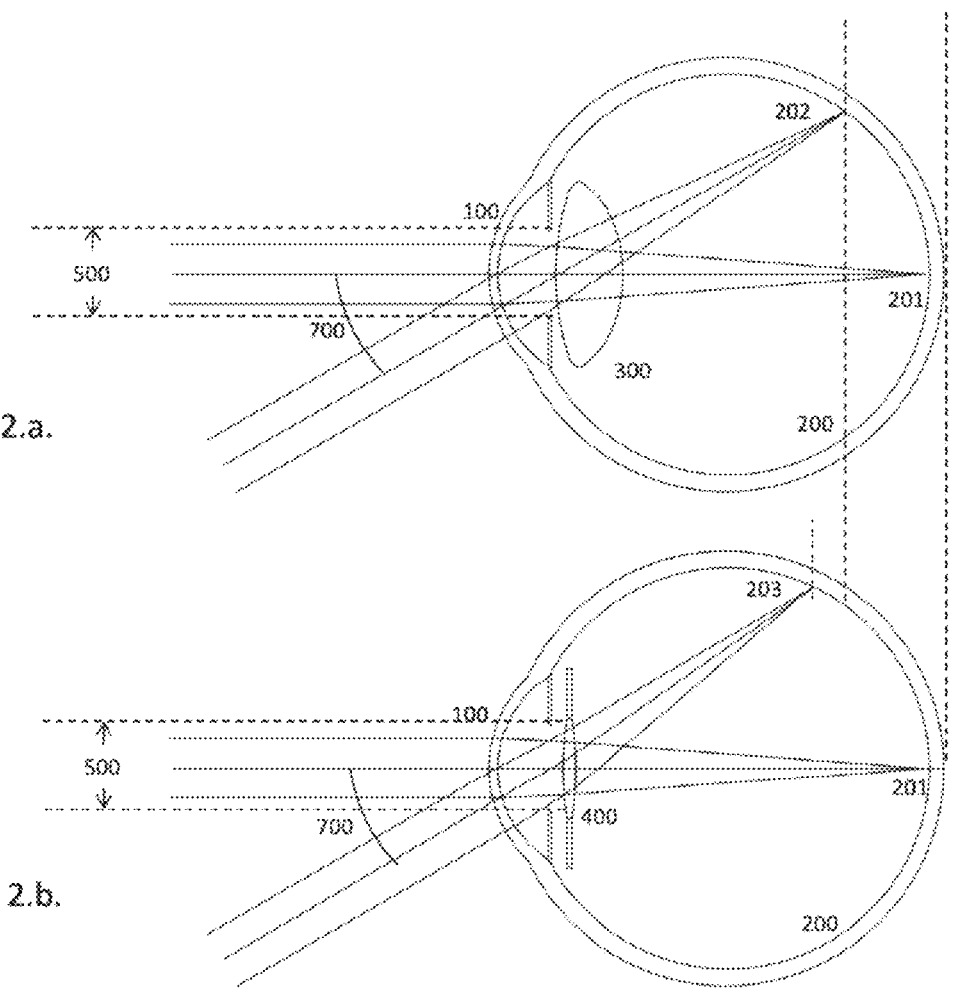
FIG. 2a shows a transversal section of the natural human eye, and the focus of objects in the center of the visual field and in the periphery of the visual field.
FIG. 2b shows a transversal section of the pseudophakic eye, that is, an eye with an intraocular lens from the prior art implanted in the posterior chamber of the eye, and the focus of objects in the center of the visual field and in the periphery of the visual field

FIG. 2a (prior art) shows a transversal section of the natural human eye. In the natural eye, light that enters through the pupil (500) passes through the cornea (100) and the eye lens (300) to focus on the retina (200). The objects situated in the center of the visual field are focused in the central part of the retina (201) while the objects situated in the periphery of the visual field, that arrive from an angle (700), are focused in a point on the peripheral part of the retina (202).

FIG. 2b (prior art) shows a pseudophakic eye, that is, an eye with an intraocular lens IOL (400) implanted in the posterior chamber. Light entering through the pupil (500) passes through the cornea (100) and the IOL (400) focusing in the retina (200). Objects located in the center of the visual field form the image in the central part of the retina (201) while objects situated in the peripheral part of the visual field, arriving from an angle (700), are focused in a peripheral point of the retina (203), generally different from the corresponding point of the natural eye (202).

Figure 3:
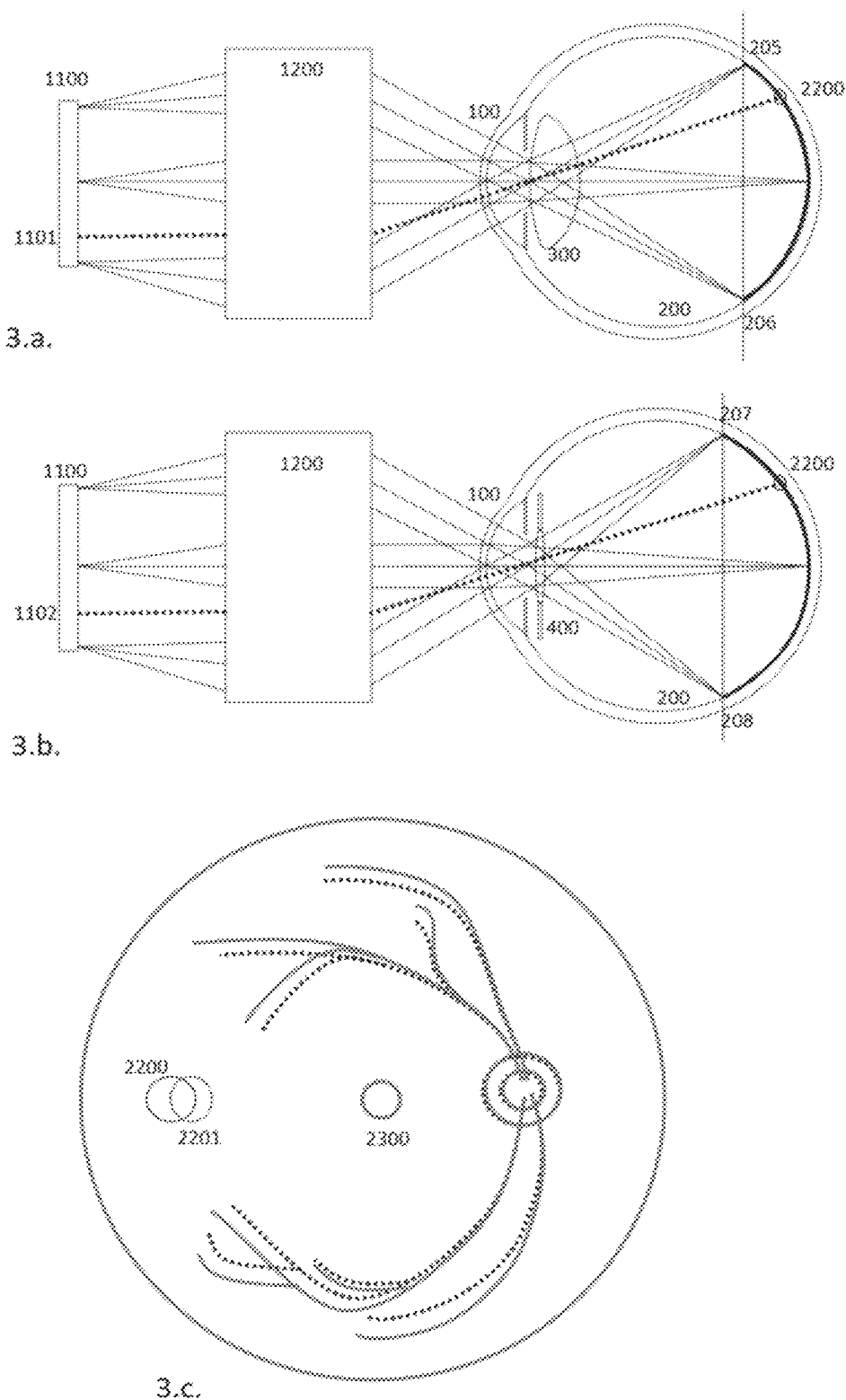
FIG. 3a shows a camera equipped with an optical system that records an image of an eye's retina through the cornea and the natural eye lens.
FIG. 3b shows a camera equipped with an optical system that records an image of an eye's retina through the cornea and an intraocular lens.
FIG. 3c shows an overlap of the images of the retina registered in the conditions shown in FIGS. 3a and 3b.

FIG. 3a (prior art) shows a camera (1100) equipped with an optical system (1200) that records an image of the retina (200) of an eye through the cornea (100) and the eye lens (300). The visual field extends over an area at the end of the eye (200) between the edges (207) and (208). The details in the retina (2200) form an image in a point of the detector (1101).

FIG. 3b (prior art) shows a camera (1100) equipped with an optical system (1200) that records an image of the retina (200) of an eye through the cornea (100) and an intraocular lens (400). The visual field extends over a larger anatomical area at the end of the eye (200) between the edges (207) and (208). The details in the retina (2200) form an image in a point of the detector (1102) that is different in general from the point corresponding to the natural eye (1101).

FIG. 3c (prior art) shows overlapped the images of the retina recorded in the conditions shown in FIGS. 3a and 3b. The dashed lines correspond to images recorded through the pseudophakic eye (FIG. 3b). The details in the retina (2200), appear displaced towards the center of the image and distorted (smaller in size) in the radial direction. In the central part of the image, the macula (2300) shows minimal or non-existent changes in size.

Figure 4:
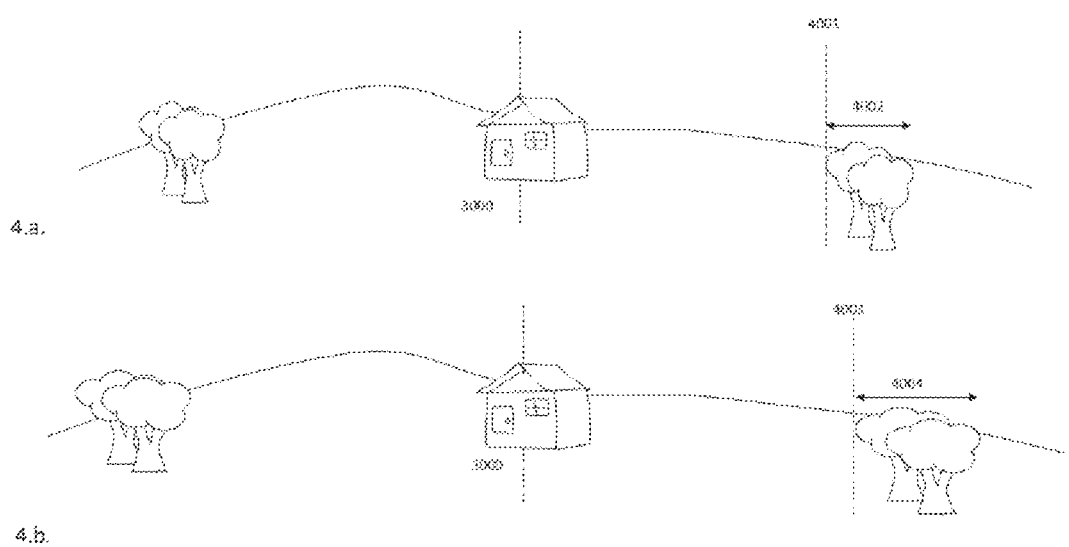
FIG. 4a shows an image of a natural scene as perceived by the natural eye.
FIG. 4b shows an image of a natural scene as perceived by a pseudophakic eye.

FIG. 4a (prior art) shows an image of a natural scene as perceived by the natural eye, in which an object is located at the center of the visual field (3000) and a peripheral object is located at an angle (4001) and has an angular size (4002).

FIG. 4b (prior art) shows the same image perceived through a pseudophakic eye. The central object (3000) has a minimal (or non-existent) change in magnification. However, the peripheral object is located at a new perceived field angle (4003) and has a different angular size (4004).

FIG. 5a shows a transversal section of the natural human eye. In the natural eye, the light that enters through the pupil (500) passes through the cornea (100) and the eye lens (300) focusing in the retina (200). The objects situated in the center of the visual field are focused in the central part of the retina (201) while objects located in the periphery of the visual field, arriving from an angle (700), are focused in a peripheral point of the retina (202).

FIG. 5b shows a pseudophakic eye, with an IOL (400) implanted in the posterior chamber. Light entering through the pupil (500) passes through the cornea (100) and the IOL (400) focusing on the retina (200). The IOL (400) has an anterior refractive element (401) and a posterior refractive element (402). The combined power of the elements (401) and (402) is suitable for a sharp focusing in the retina (200). Objects located in the center of the visual field are focused in the central part of the retina (201) while objects located in the periphery of the visual field, arriving from an angle (700), are focused on a point of the peripheral part of the retina (203). The balance of powers between the anterior element (401) and the posterior element (402) is such that the nodal point of the eye does not change when implanting the IOL (400) and the peripheral position in the retina (203) is very close to the corresponding point of the natural eye (202), as can be seen when comparing FIGS. 5a and 5b.

Figure 6:
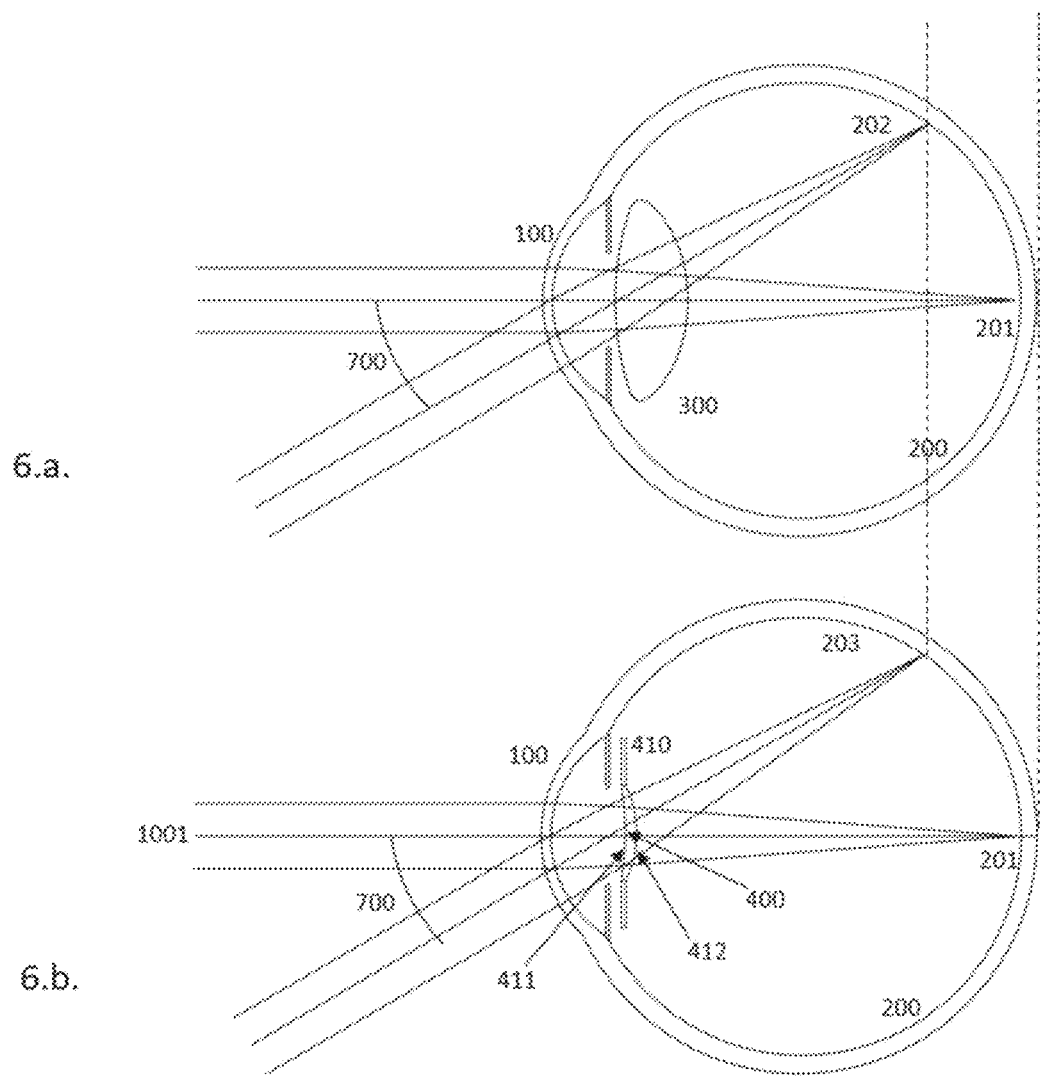
FIG. 6a shows a transversal section of a human eye and the focus of objects in the center of the visual field and with certain angle in the periphery of the visual field.
FIG. 6b shows a pseudophakic eye, with another intraocular lens of the invention implanted in the posterior chamber.

FIG. 6a shows a transversal section of the natural human eye. In the natural eye, light that enters through the pupil (500) passes through the cornea (100) and the eye lens (300) and focuses in the retina (200). Objects located in the center of the visual field are focused in the central part of the retina (201), while objects located in the peripheral part of the visual field, arriving from an angle (700), are focused in a point in the peripheral part of the retina (202).

FIG. 6b shows a preferred embodiment of the present invention where an intraocular lens (400) has an anterior surface with negative power (411), a posterior surface with positive power (412) and a haptics portion (410). The power balance between the anterior element (401) and the posterior element (402) is such that the nodal point of the eye does not change when implanting an IOL (400) and the peripheral position in the retina (203) is very close to the corresponding point in the natural eye (202). In this embodiment, even when the haptics portion (410) is implanted in the lens capsule as in every intraocular lens, the optical power of the IOL (400) is distributed over the optical axis of the eye (1001) such that the peripheral rays have a minimal or non-existent distortion.

Figure 7:
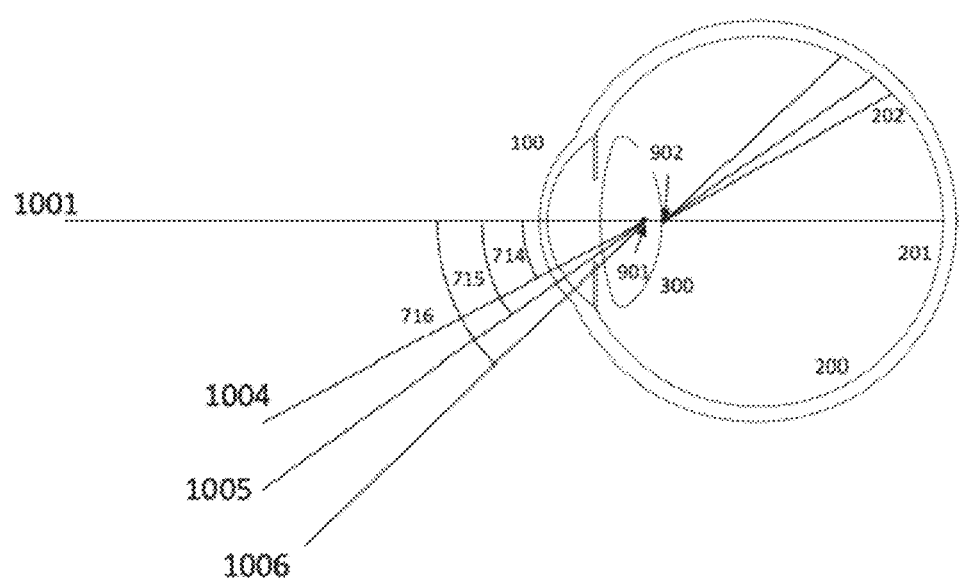
FIG. 7 shows a transversal section of an eye and a plurality of rays that enter the optical system both on the optical axis and forming different angles with respect to the optical axis.

FIG. 7 shows a transversal section of an eye and a plurality of rays that enter the optical system both over the axis (1001) and peripherally (1004, 1005, 1006) forming different angles (714, 715, 716) with the optical axis. Suitable methods are employed such as Optical Coherence Tomography (OCT) and corneal topography to measure the anatomical dimensions of the eye over these orientations as well as the refractive power of the cornea over said axes. Off-axis biometry data are used to estimate the shape of the retina fitting mathematically a generical aspherical surface that passes through the measured points. The combined biometry, topography and refractive data form an over-determined system that can be solved to obtain the shape of the retina and the nodal points of the eye through any of the mathematical methods known to solve said problems. The distance S, defined in FIG. 8a, can then be obtained for any field angle given by simple geometrical considerations related to the known shape of the retina and the angle of the incident light. The anatomy of the anterior segment of the eye is used to predict the post-operative depth at which the intraocular lens will be implanted. Axial length measurements of the eye are used, as well as measurements of the shape of the retina (200), to calculate the appropriate balance of powers in the anterior and posterior surfaces of the intraocular lens to maintain the geometrical relation between the object and image space (S, in FIGS. 8a and 8c). This calculation is essentially an optimization of multiple parameters, something common in the optical design art through ray tracing. In this case, the parameters are the anterior and posterior powers (or, equivalently, the anterior and posterior radii of curvature if the index of refraction of the material of the lens is known), while the optimization objectives include the focus on axis and the size of the image for each field angle. The size of the desired image can be calculated directly from the shape of the retina as described previously.

The periphery of the visual field after cataract surgery suffers from geometrical distortion. This means, also referencing FIG. 3, that images of the end of the eye recorded through optical instruments will suffer from distortion, meaning that the position of the retinal features will appear altered and the shape of said features will be affected in the radial direction.

Also, with reference to FIGS. 4a and 4b, after cataract surgery the peripheral objects will appear with different eccentricity compared to the ones that appear before the operation. Besides peripheral objects appearing further away in the periphery, their shape will appear radially elongated.

In the present invention the intraocular lens (IOL) design of posterior chamber approximates the geometrical properties of the image of the natural eye lens, specially with respect to the distortion of an image in the far periphery of the visual field. The IOL is manufactured from one of the existent suitable materials for intraocular implantation such as hydrophobic acrylic, silicone and may be produced both by machining as by molding.

The IOL has a central part with an approximate diameter of 6 mm with the desired optical properties, and a peripheral part that extends to a diameter between 10 and 14 mm (the haptics portion) that helps to center and stabilize the IOL in the lens capsule once the nucleus and the cortex of the cataract lens are extracted. The lens haptics do not belong to the context of the present invention and is selected from a range of designs stablished in the scientific literature in the last 50 years. For surgery, the IOLs are folded and injected in the lens capsule prepared through a small incision in the eye's limbus or the peripheral cornea.

In the preferent embodiment of the IOL, it is manufactured molding hydrophobic acrylic material with a refraction index of approximately 1.53. With reference to the FIG. 6b, the anterior surface (401) of the IOL is an aspheric concave surface and the posterior surface (402) is aspheric convex. The optical portion of the lens is circular and has a diameter of approximately 6 mm. The anterior surface (401) has negative refractive power when submerged in the aqueous humor of the eye while the posterior surface (402) has positive refractive power. These two surfaces combined produce a refractive power on the order of 20D when submerged in the aqueous humor of the eye (or similar aqueous solution such as saline). The exact power can be selected from a variety of anterior curvatures (401) and posterior curvatures (402) in order to provide the required power of the eye in question, based on its axial length, corneal power and anticipated depth of implantation. One or both of these surfaces can have an appropriate conic constant to correct spherical aberration of the cornea or to introduce different amounts of spherical aberration. The form factor of a positive meniscus with concave anterior surface results in a lens implanted in the capsule having its principal plane at a larger depth in the eye than the physical depth defined by its haptics portion. As a result, the properties of the image in the periphery are similar to those of the natural eye in which the posterior surface of the eye lens has a significant fraction of the power of the lens and is generally located at a larger depth with respect to intraocular lenses. To control even more the functional depth at which the IOL is implanted, its physical depth can be increased by incorporating a small tilt in the haptics of the order of between 2 and 10 degrees.

Figure 5:
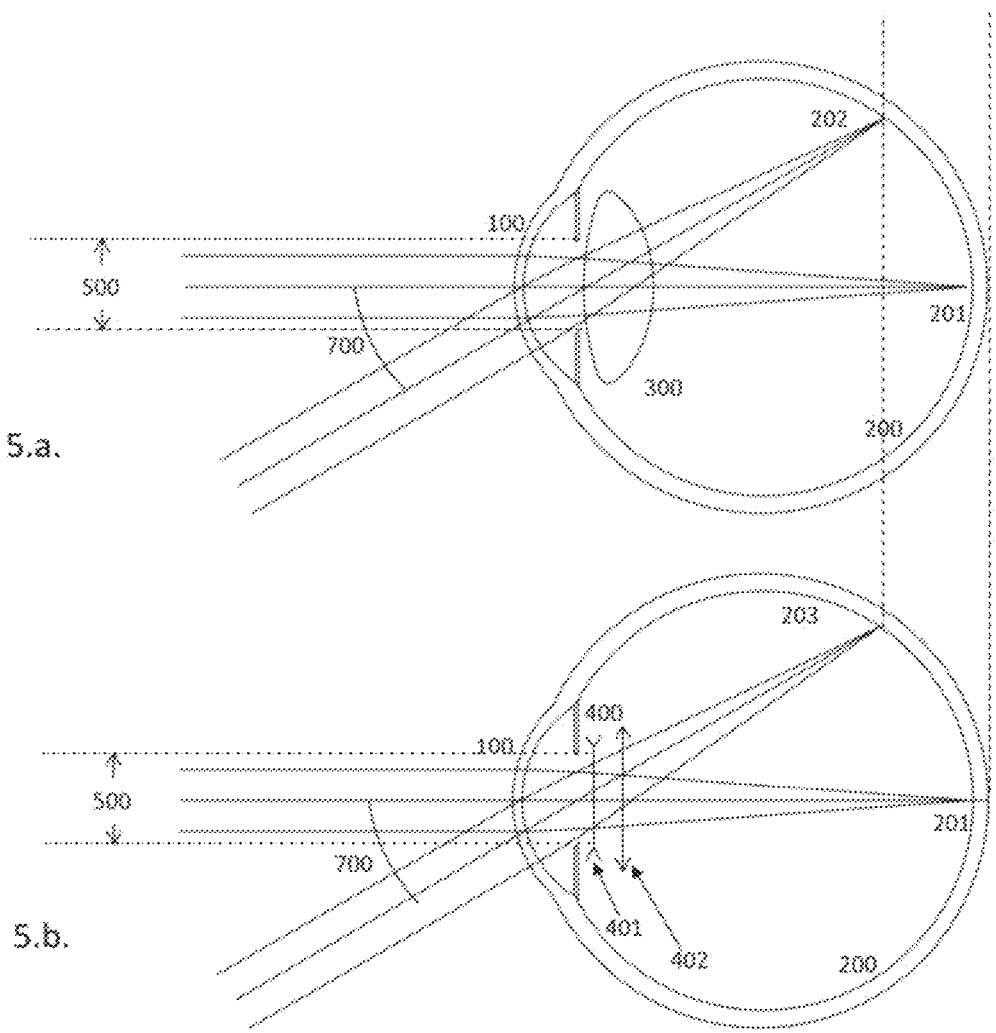
FIG. 5a shows a transversal section of the human eye and the focus of objects in the center of the visual field and with certain angle in the periphery of the visual field.
FIG. 5b shows a pseudophakic eye, with an intraocular lens of the invention implanted in the posterior chamber.

Another preferent embodiment of the IOL is a combination of the two separated optical elements. Both elements are manufactured both by machining and by molds with hydrophobic acrylic material with a refractive index between 1.46 and 1.55 approximately. With reference to FIG. 5, the anterior element (401) of the IOL is a negative lens (shown schematically) while the posterior element (402) is a positive lens (shown schematically). The optical portion of the lens is circular and has a diameter between 5 and 7 mm approximately. These two elements combined produce a refractive power of the order of 20D when submerged in the aqueous humor of the eye (or a similar aqueous solution such as saline). A fixed spacing between the anterior and posterior elements control the position of the cardinal points of the lens and therefore the nodal points of the eye. In a preferred embodiment both elements are in contact with their edges and their separation allows it to be filled with aqueous solution during its implantation. In another preferred embodiment both elements are in contact and the spatial separation of their optical surfaces is determined by their thickness. In this embodiment, the power balance between the two elements is adjusted to control the position of the cardinal points of the intraocular lens system and therefore the nodal points of the pseudophakic eye. In this case, as indicated in the present embodiment where the anterior element has negative power and posterior element has positive power, the intraocular lens is equivalent to the implanted lens at a larger depth in the eye than the physical depth defined by its haptics portion (in the capsule). As a result, the properties of the image in the periphery are similar to those of the natural eye in which the posterior surface of the lens of the natural eye has a significant fraction of the power of the lens and is located generally at a larger depth with respect to the intraocular lenses.

In a preferred embodiment the lens is designed and adapted to the individual eye, personalized in terms of the image properties in the close and far periphery. For this purpose and in reference to FIG. 7, the eye's anatomy is measured with suitable methods such as Optical Coherence Tomography (OCT) or a special biometer or peripheral wavefront sensor. The ocular shape, both of its anterior segment (cornea, anterior chamber, iris) as well as its axial length is measured over the different orientations. These measurements, in combination with refractive and aberration measurements of the eye over the previously mentioned orientations, are used to create a wide-angle optical model of the particular eye. The model is used to calculate the optical properties of the intraocular lens with respect to the magnification both on-axis and off-axis. The mean power of the lens is determined with a standard IOL calculation for emmetropia on-axis. For the periphery, the design of the intraocular lens, having the power balance between the two elements as a free parameter, is adjusted so that the peripheral magnification fits with the (proportionated) intact eye.

In a preferred embodiment the intraocular lens is formed by two separated optical elements. In another preferent embodiment the intraocular lens is a meniscus with negative anterior power and positive posterior power, where the power balance is adjusted following the calculations described previously. In another preferent embodiment the intraocular lens has the shape of a positive meniscus optimized for the peripheral magnification/distortion using anatomical and refractive data from the literature. In this preferent embodiment, the resulting lens would perform better than a conventional IOL for the average eye, but its form factor would not be personalized for each individual eye.

Figure 8:
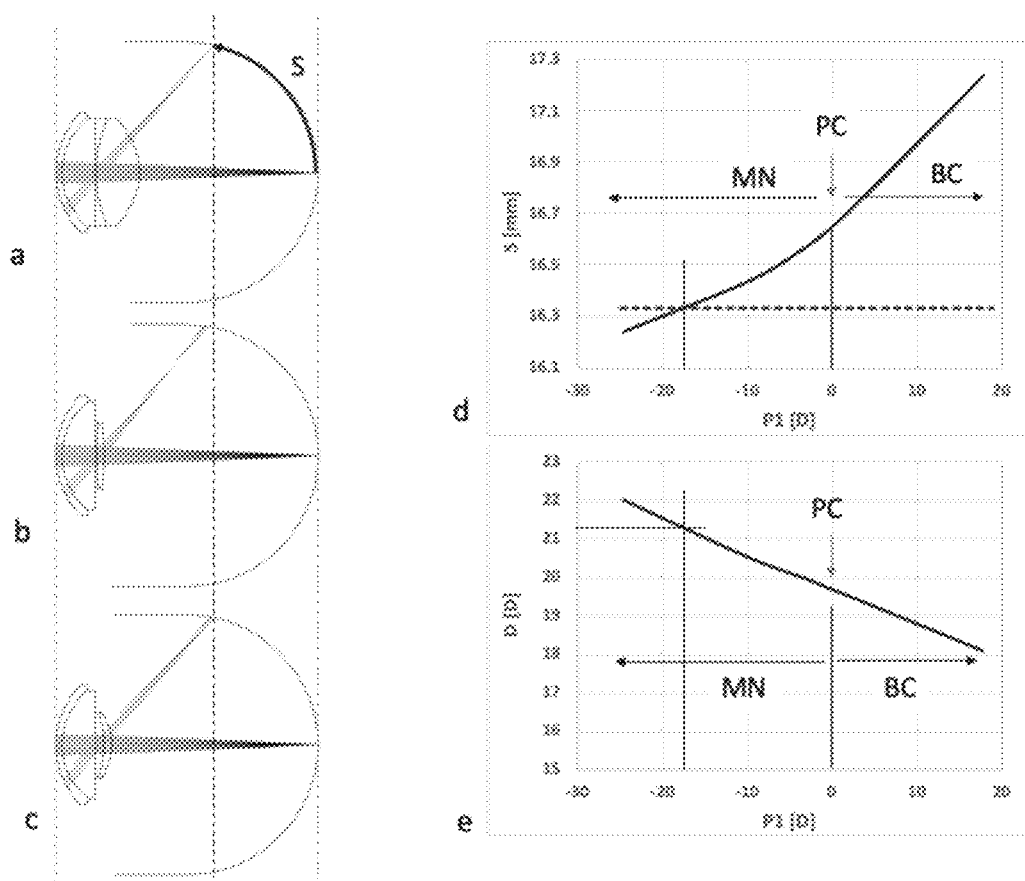
FIG. 8a shows a normal eye that focuses entering light in the center of the visual field while the peripheral rays of a field at 60 degrees (visual angle) are focused in a peripheral area of the retina.
FIG. 8b shows a pseudophakic eye with a standard biconvex intraocular lens that focuses entering light in the center of the visual field while the peripheral rays of a field at 60 degrees (visual angle) are focused in a peripheral area of the retina.
FIG. 8c shows a pseudophakic eye with an intraocular lens obtained through the method of the present invention in which the eye is focusing entering light in the center of the visual field while the peripheral rays of a field at 60 degrees (visual angle) are focused in a peripheral area of the retina.
FIG. 8d shows the result of a ray tracing analysis using the refractive power D of the anterior surface of the intraocular lens as a free parameter.
FIG. 8e shows the result of a ray tracing analysis using the refractive power D of the anterior surface of the intraocular lens as a free parameter.

FIGS. 8a and 8d show how the power balance between anterior and posterior surfaces of an intraocular lens provides the control of the location in the retina of the peripheral objects and the associated ray tracing calculations.

FIG. 8a shows a normal eye that focuses incident light in the center of the visual field while the peripheral rays from a field at 60 degrees (visual angle) are focused on a peripheral area of the retina at a distance S of the optical axis.

FIG. 8b shows a pseudophakic eye with a standard biconvex intraocular lens that focuses incident light in the center of the visual field while peripheral rays from a field at 60 degrees (visual angle) are focused in a peripheral area of the retina at a distance of the optical axis generally larger than S.

FIG. 8c shows a pseudophakic eye with a modified intraocular lens according to the present invention in which the eye is focusing incident light in the center of the visual field while the peripheral rays from a field at 60 degrees (visual angle) are focused on a peripheral area of the retina at a distance from the optical axis substantially equal to S.

In FIG. 8d the result of a ray tracing analysis that uses the refractive power of the anterior surface of the intraocular lens as a free parameter is shown. For each established parameter of the anterior surface's power, the refractive power of the posterior surface is adjusted in order to provide a suitable focus for the incident light over the axis. The horizontal axis refers to the refractive power of the anterior surface while the vertical axis shows the value of the resulting distance S (as defined in FIG. 8a). When the power of the anterior surface is negative the lens is a meniscus (area shown as MN), when the anterior power is zero the lens is plano-convex (indicated as PC) and when the anterior power is positive the lens is biconvex (area shown as BC).

The dashed line refers to the typical value S for a normal eye, as shown in FIG. 8a. From the calculations it follows that to keep the same S after the implantation of an IOL the power of the anterior surface must be of approximately −17D while the power of the posterior surface must be increased in consequence, such that the total power of the lens is approximately 20D, which is what it is required for a proper focusing on the axis.

The real value of the distance S as well as the total power of the IOL will change depending on the anatomy of the eye.

FIG. 8e shows the result of a ray tracing analysis that uses the refractive power of the anterior surface of the intraocular lens as a free parameter. For each stablished value for the anterior surface power, the refractive power of the posterior surface is adjusted in order to provide a suitable focus for the incident light on-axis. The horizontal axis refers to the refractive power of the anterior surface while the vertical axis shows the total power of the IOL to maintain a proper focus on the optical axis. When the power of the anterior surface is negative, the lens is a meniscus (area shown as MN), when the anterior power is zero the lens is plane-convex (indicated as PC) and when the power of the anterior surface is positive the lens is biconvex (area shown as BC). As an example, if a determined eye requires a biconvex lens of 19 diopters (anterior power equal to 9.5 diopters) and a meniscus is designed to maintain the value S constant, then the anterior surface of the lens will have a power of −17D (as in FIG. 8d) and the total power of said meniscus will be approximately 21.3 diopters. The real value of S as well as the total power of the IOL will change depending on the anatomy of the eye.

According to another embodiment of the method of invention the calculation of the length S for each field angle (714, 715, 716) is realized in an eye model corresponding to an average physiological eye, as an approximation of the patient's eye.

Although several embodiments of the invention have been depicted and described, it is evident that modifications contained in its scope can be introduced, and it must not be considered limited to said embodiments, but only to the content of the following claims.

The invention claimed is:

1. Method to design and manufacture an intraocular lens, comprising an optical part and a haptics part, in which the optical part comprises an anterior surface with negative refractive power and a posterior surface with positive refractive power, the anterior surface being the closest to the eye's cornea once implanted the lens in the eye, and the posterior surface being the closest to the eye's retina once implanted the lens in the eye, that comprises the following steps:
   to provide the haptics part,
   to provide the optical part, and
   to join the haptics part with the optical part,
   wherein in order to determine the refractive power D of the anterior surface of the optical part and the refractive power D' of the posterior surface of the optical part the following steps are performed:
   a plurality of light rays are provided over the normal eye, both on its optical axis and off the optical axis forming different angles with respect to the optical axis,
   for each light ray with its angle the axial length of the eye is measured, including the intersecting point of the light ray with the eye's retina, and the refractive power of the cornea,
   determination of the shape of the retina from said measurements for light rays that are on the optical axis and light rays that are off the optical axis using a mathematical fit to an aspherical surface that contains the measured points,
   calculation of the arc length S that goes from the intersection of the optical axis with the retina of the eye until the intersection of the light ray with the retina of the eye for each angle, as a function of the shape of the retina and the angle of the light ray, and
   fit of the refractive power D of the anterior surface of the optical part and the refractive power D' of the posterior surface of the optical part using ray tracing optimization in a model of pseudophakic eye, to provide both an optical focus for the central vision on the optical axis as well as a length S for each field angle, so that they are like those in the normal eye and utilizing said measurements for on-axis and off-axis rays obviate distortions of peripheral images on the retina.

2. Method to design and manufacture an intraocular lens according to claim 1, in which the calculation of the length S for each field angle is realized in an eye model corresponding the average physiological eye as an approximation of the patient's eye.

3. Method to design and manufacture an intraocular lens according to claim 1, in which the intraocular lens is manufactured by molding.

4. Method to design and manufacture an intraocular lens according to claim 1, in which the intraocular lens is manufactured by machining.

5. Method to design and manufacture an intraocular lens according to claim 2, in which the intraocular lens is manufactured by molding.

6. Method to design and manufacture an intraocular lens according to claim 2, in which the intraocular lens is manufactured by machining.

* * * * *